US00PP15653P2

(12) United States Plant Patent
Hanes

(10) Patent No.: US PP15,653 P2
(45) Date of Patent: Mar. 15, 2005

(54) ***GERANIUM* PLANT NAMED 'CANTE CORAS'**

(50) Latin Name: *Pelargonium×hortorum×Pelargonium tongense*
Varietal Denomination: Cante Coras

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 5 days.

(21) Appl. No.: 10/818,502

(22) Filed: Apr. 5, 2004

(51) Int. Cl.[7] ..... A01H 5/00
(52) U.S. Cl. ..... Plt./324
(58) Field of Search ..... Plt./324

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Cante Coras', characterized by its upright, outwardly spreading and mounded growth habit; freely basal branching habit; dark green-colored leaves; freely flowering habit with many flower umbels per plant; flower umbels with numerous coral red-colored single flowers; and resistance to leaf oedema.

1 Drawing Sheet

Botanical classification/cultivar designation: *Pelargonium×hortorum×Pelargonium tongense* cultivar Cante Coras.

BACKGROUND OF THE INVENTION

The present invention relates to a new and distinct cultivar of *Geranium* plant, botanically known as *Pelargonium×hortorum×Pelargonium tongense,* commercially known as an interspecific *Geranium*, and hereinafter referred to by the name 'Cante Coras'.

The new *Geranium* is a product of a planned breeding program conducted by the Inventor in Gilroy, Calif. The objective of the breeding program is to develop new *Geranium* cultivars with mounded plant habit, good basal branching, large flowers, attractive flower and foliage coloration and resistance to leaf oedema.

The new *Geranium* originated from a cross-pollination made by the Inventor in October, 1996 of a proprietary *Pelargonium×hortorum×Pelargonium tongense* selection identified as code number 6271-5, not patented, as the female, or seed, parent with a proprietary *Pelargonium×hortorum×Pelargonium tongense* selection identified as code number 6828-5, not patented, as the male, or pollen, parent. The cultivar Cante Coras was discovered and selected by the Inventor as a flowering plant within the progeny from this cross-pollination in a controlled environment in Gilroy, Calif. in March, 1997.

Asexual reproduction of the new cultivar by terminal cuttings at Gilroy, Calif., since March, 1997 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Cante Coras'. These characteristics in combination distinguish 'Cante Coras' as a new and distinct *Geranium* cultivar:

1. Upright, outwardly spreading and mounded growth habit.
2. Freely basal branching habit.

3. Dark green-colored leaves.
4. Freely flowering habit with many flower umbels per plant.
5. Flower umbels with numerous coral red-colored single flowers.
6. Resistant to leaf oedema.

In side-by-side comparisons conducted in Gilroy, Calif., plants of the new *Geranium* differed from plants of the female parent selection in the following characteristics:

1. Plants of the new *Geranium* were more vigorous than plants of the female parent selection.
2. Plants of the new *Geranium* had darker green-colored leaves than plants of the female parent selection.
3. Plants of the new *Geranium* and the female parent selection differed in flower color as plants of the female parent selection had red-colored flowers.

In side-by-side comparisons conducted in Gilroy, Calif., plants of the new *Geranium* differed from plants of the male parent selection in the following characteristics:

1. Plants of the new *Geranium* had darker green-colored leaves than plants of the male parent selection.
2. Plants of the new *Geranium* and the male parent selection differed in flower color as plants of the male parent selection had red-colored flowers.

The new *Geranium* can be compared to the cultivar, Balgalsusi, disclosed in U.S. Plant Pat. No. 12,474. However, in side-by-side comparisons conducted in Gilroy, Calif., plants of the new *Geranium differed from plants of the cultivar Balgalsusi in the following characteristics:*

1. Plants of the new *Geranium* were more densely foliated than plants of the cultivar Balgalsusi.
2. Plants of the new *Geranium* had shorter peduncles than plants of the cultivar Balgalsusi.
3. Flowers of plants of the new *Geranium* were lighter in color than flowers of plants of the cultivar Balgalsusi.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Cante Coras'.

The photograph at the bottom of the sheet is a close-up view of typical flowers and leaves of 'Cante Coras'.

Flower and foliage colors in the photographs may differ slightly from the color values cited in the detailed botanical description which accurately describe the colors of the new *Geranium*.

DETAILED BOTANICAL DESCRIPTION

Plants of the cultivar Cante Coras have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the late spring with day temperatures about 27 to 29° C., night temperatures about 16 to 18° C. and light levels about 2,000 foot-candles. Plants used for the photographs and description were about five months from planting rooted cuttings. In the following description, color references are made to The Royal Horticultural Society Colour Chart, 1995 Edition, except where general terms of ordinary dictionary significance are used.

Botanical classification: *Pelargonium×hortorum×Pelargonium tongense* cultivar Cante Coras.

Parentage:

*Female parent.*—Proprietary *Pelargonium×hortorum×Pelargonium tongense* selection identified as code number 6271-5, not patented.

*Male parent.*—Proprietary *Pelargonium×hortorum×Pelargonium tongense* selection identified as code number 6828-5, not patented.

Propagation:

*Type cutting.*—Terminal cuttings.

*Time to initiate roots.*—About 12 to 14 days at 22° C.

*Time to develop roots.*—About 25 to 30 days at 22° C.

*Root description.*—Fibrous; white in color.

*Rooting habit.*—Freely branching.

Plant description:

*General appearance.*—Upright, outwardly spreading and mounded growth habit.

*Growth and branching habit.*—Vigorous and very freely basal branching with about eleven lateral branches per plant. Pinching, that is, removal of terminal apices, is typically not required.

*Plant height to top of foliage.*—About 17 cm.

*Plant height to top of flower umbels.*—About 30 cm.

*Plant width.*—About 44 cm.

*Lateral branches.*—Length: About 24 cm. Diameter: About 5 mm. Internode length: About 3.5 cm. Texture: Pubescent. Color: 144A.

*Foliage description.*—Arrangement: Alternate, simple; after flowering, opposite. Length: About 7.5 cm. Width: About 8 cm. Shape: Rounded reniform. Apex: Rounded. Base: Cordate. Margin: Crenate with about seven lobes. Venation: Palmate. Texture, upper and lower surfaces: Slightly coarse; glandular; pubescent. Color: Developing foliage, upper and lower surfaces: 146A. Fully expanded foliage, upper surface: 147A. Fully expanded foliage, lower surface: 147B. Venation, upper surface: 146C. Venation, lower surface: 147C. Petiole: Length: About 9 cm. Diameter: About 2 mm. Texture, upper and lower surfaces: Pubescent. Color, upper and lower surfaces: 144A.

Flower description:

*Flower arrangement and type.*—Single rounded flowers arranged in hemispherical umbels arising from apical leaf axils. Umbels displayed above the foliage. At full flowering, usually about 24 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 5 cm. Diameter: About 8 cm. Number of flowers and flower buds per umbel: About 22. Flower diameter: About 4 cm. Flower depth (height): About 2.3 cm.

*Flower buds.*—Length: About 1.5 cm. Diameter: About 6 mm. Shape: Ovoid. Color: 45B.

*Petals.*—Quantity/arrangement: About five petals per flower in a single whorl. Length: About 2.2 cm. Width, upper two petals: About 1.3 cm. Width, lower three petals: About 1.5 cm. Shape: Obovate to slightly spatulate. Apex: Rounded. Base: Attenuate. Margin: Entire. Texture, upper and lower surfaces: Smooth; satiny. Color: When opening, upper surface: Slightly more pink than 45B. When opening, lower surface: 46C. Fully opened, upper two petals, upper surface: 50A; towards the base, 45C; at the base, 155D; venation, 67A. Fully opened, lower three petals, upper surface: 50A; at the base, 155D; venation, similar to petal color. Fully opened, upper two petals, lower surface: 50B; at the base, 155D; venation, 67B. Fully opened, lower three petals, lower surface: 50B; at the base, 155D; venation, similar to petal color.

*Sepals.*—Quantity/arrangement: Five per flower in a single whorl; not imbricate on open flowers. Length: About 1.3 cm. Width: About 3 mm. Shape: Elliptical. Apex: Acuminate. Margin: Entire. Texture, upper and lower surfaces: Smooth; glabrous. Color, upper and lower surfaces: 144A.

*Peduncle* (*umbel stem*).—Length: About 20 cm. Diameter: About 2.5 mm. Angle: About 45° from vertical. Strength: Strong. Texture: Pubescent. Color: 144A.

*Pedicel* (*individual flower stem*).—Length: About 2.7 cm. Diameter: About 1 mm. Angle: About 20 to 45° from vertical. Strength: Strong. Texture: Pubescent. Color: 144A.

*Reproductive organs.*—Androecium: Anther quantity: About ten per flower. Anther size: About 1 by 2 mm. Anther shape: Oval. Anther color: 57B. Pollen amount: Scarce. Pollen color: 42B. Gynoecium: Pistil quantity: One per flower. Pistil length: About 9 mm. Stigma shape: Five-parted, star-shaped; reflexed. Stigma color: 53C. Style length: About 1.5 mm. Style color: 158A. Ovary color: 194C.

*Seed/fruit.*—Seed and fruit development has not been observed.

Disease/pest resistance: Resistance to pathogens and pests common to *Pelargonium* has not been observed.

Oedema resistance: Plants of the new *Geranium* have been observed to be resistant to leaf oedema when exposed to conditions conducive to leaf oedema development.

It is claimed:

1. A new and distinct cultivar of *Geranium* plant named 'Cante Coras', as herein illustrated and described.

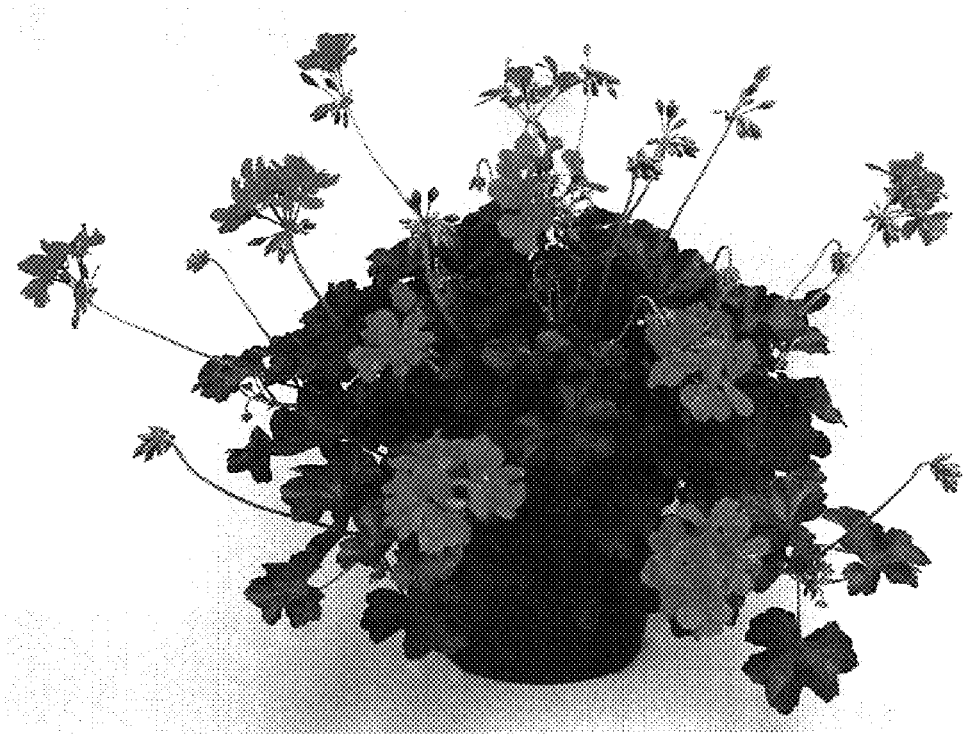
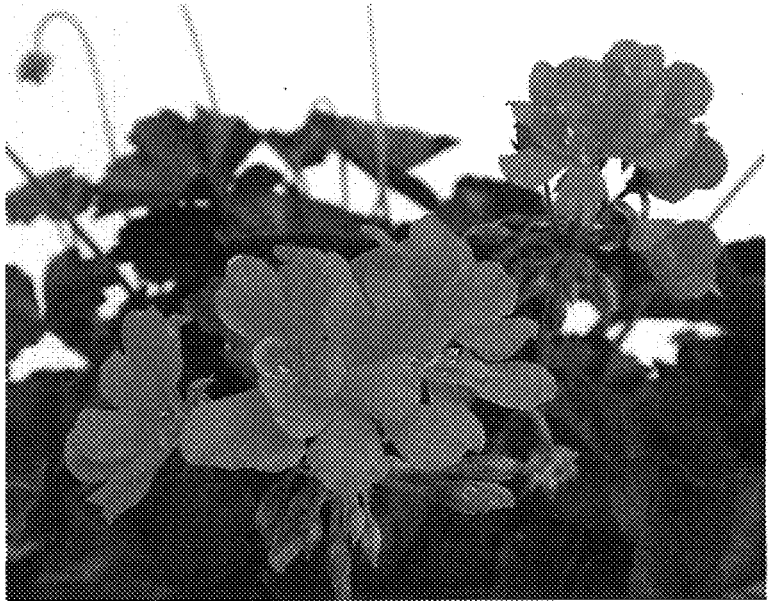

* * * * *